(12) United States Patent
Colombo et al.

(10) Patent No.: US 6,821,233 B1
(45) Date of Patent: Nov. 23, 2004

(54) DEVICE AND METHOD FOR AUTOMATING TREADMILL THERAPY

(75) Inventors: Gery Colombo, Zurich (CH); Matthias Joerg, Stafa (CH); Peter Hostettler, Oberweil (CH)

(73) Assignee: Hocoma AG, Volketswil (CH)

( * ) Notice: Subject to any disclaimer, the term of this patent is extended or adjusted under 35 U.S.C. 154(b) by 0 days.

(21) Appl. No.: 09/831,639

(22) PCT Filed: Nov. 11, 1999

(86) PCT No.: PCT/CH99/00531

§ 371 (c)(1),
(2), (4) Date: Jul. 20, 2001

(87) PCT Pub. No.: WO00/28927

PCT Pub. Date: May 25, 2000

(30) Foreign Application Priority Data

Nov. 13, 1998 (CH) .............................................. 2285/98

(51) Int. Cl.[7] .......................... A63B 24/00; A61F 5/00; G09B 3/00
(52) U.S. Cl. ............................. 482/54; 602/23; 607/49; 482/69
(58) Field of Search .............................. 482/51, 66, 54, 482/69; 602/16, 36, 23; 601/23, 33, 35; 434/255, 307 R; 607/49

(56) References Cited

U.S. PATENT DOCUMENTS

| | | | | |
|---|---|---|---|---|
| 4,697,808 A | * | 10/1987 | Larson et al. | 482/51 |
| 4,969,452 A | * | 11/1990 | Petrofsky et al. | 602/16 |
| 5,020,790 A | * | 6/1991 | Beard et al. | 482/4 |
| 5,054,476 A | * | 10/1991 | Petrofsky et al. | 602/16 |
| 5,135,469 A | * | 8/1992 | Castillo | 602/16 |
| 5,476,441 A | * | 12/1995 | Durfee et al. | 602/23 |
| 5,502,851 A | * | 4/1996 | Costello | 5/86.1 |
| 5,588,841 A | * | 12/1996 | Mechling | 434/255 |
| 5,954,621 A | * | 9/1999 | Joutras et al. | 482/114 |
| 5,961,476 A | * | 10/1999 | Betto et al. | 602/16 |
| 5,961,541 A | * | 10/1999 | Ferrati | 607/49 |

* cited by examiner

Primary Examiner—Stephen R. Crow
(74) Attorney, Agent, or Firm—Burns, Doane, Swecker & Mathis, L.L.P.

(57) ABSTRACT

The invention relates to an automatic machine, which is used in treadmill therapy (walking therapy) of parapetic and hemiparetic patients. The machine automatically guides the patient's legs on the treadmill. The machine includes a driven and controlled orthotic device, which guides the legs in a physiological pattern of movement, a treadmill and a relief mechanism. Knee and hip joints of the orthotic device each include a drive. The orthotic device is stabilized on a treadmill with stabilizing means in such a manner that the patient does not have to keep his/her equilibrium. The othotic device can be adjusted in height and can be adapted to different patients.

16 Claims, 9 Drawing Sheets

DEVICE AND METHOD FOR AUTOMATING TREADMILL THERAPY

The invention relates to an apparatus and a method for automating treadmill therapy for rehabilitating walking-disabled patients.

During treadmill therapy, patients (e.g., paraparetic patients or patients after a stroke) are trained on a treadmill. For this purpose, they are suspended on a special suspension device above the treadmill. On the one hand, this makes it possible to relieve part of their body weight and otherwise they need to be concerned only a small amount about maintaining their balance. Especially during the initial time after the injury, the patient is often not able at all to move his legs himself. As a result, physiotherapists must keg guide the patients' legs. If intensive training is performed on the patients as soon as possible after injury, special movement centers in the spinal chord of the patient are trained again, and the patient will learn to walk better than is possible with conventional forms of therapy. This guidance of the legs is very exhausting work for the therapists, and they tire relatively quickly when performing this training. Because of this, the training units often are too short, and the results of the therapy are less than optimal.

This training can be automated with the machine described here. This machine is an orthotic device driven at the knee and hip joints, which can be adapted to any patient. During training, the legs of the patient are guided by the orthotic device in a physiological sequence of movement. In contrast to the manually guided therapy, greater success can be achieved with the automated therapy because the training units can be performed as long as desired. It is possible to perform intensive training very soon after the patient is injured. Therapy with the driven orthotic device also requires only one therapist to caring for the patient, i.e., less personnel is needed.

Treadmill therapy is now commonly used in many areas when treating patients with neurological diseases. It is especially often used in paraplegic centers, and has been scientifically proven in this context. Therapy currently takes place on a treadmill where the patients are suspended with a belt, and their legs are guided by two physiotherapists (I. Wickelgren, Teaching the spinal cord to walk, Science, 1998, Vol. 279, 319–321). With the help of regular treadmill training, paraparetic patients and patients after a stroke are able to relearn walking much faster and better. Different orthotic devices are already being used in the rehabilitation of patients who have movement restrictions of the legs. Passive walking orthotic devices as described, for example, in U.S. 5,320,590 (1994), are already being used regularly in the rehabilitation of paraplegics. There are already several approaches for driven orthotic devices. U.S. Pat. No. 5,020,790 (1991) and GB 2260495 (1991) describe some of these, in which knee and hip joints are driven with hydraulic cylinders or electric motors. By using these orthotic devices, it is possible to move the legs of a patient for whom the respective orthotic device has been specifically manufactured in a movement pattern similar to walking.

Patent application EP 0782843 A2 (1996) describes an orthotic device that is also driven at the knee and hip joints. However, the patient undergoes his training on a treadmill. The leg movements are controlled via switches that the patient manually activates during walking and which bring about an extension or flexion of the leg.

It is the task of the invention at hand to automate the previously manual treadmill training for patients in rehabilitation.

According to the invention, this objective is realized with a driven orthotic device and an associated method for operating the orthotic device as described herein.

At issue is the guidance of the legs of a patient positioned above the treadmill in a walking pattern that as is as physiological as possible. This requires a control of the drives that regulate these drives according to a predetermined sequence of movement. The patient should be stabilized on the treadmill in such a way that he need not be concerned about his balance. This means he can concentrate on a dynamic, physiological walking pattern.

The orthotic device should be usable in the rehabilitation centers for training different patients and therefore must be adjustable in size and shape. The orthotic device must be designed so that no pressure points can be created on the patient's body since paraplegics, in particular, quickly develop pressure ulcers.

The invention is explained in more detail below in reference to the drawings.

Figure 1:
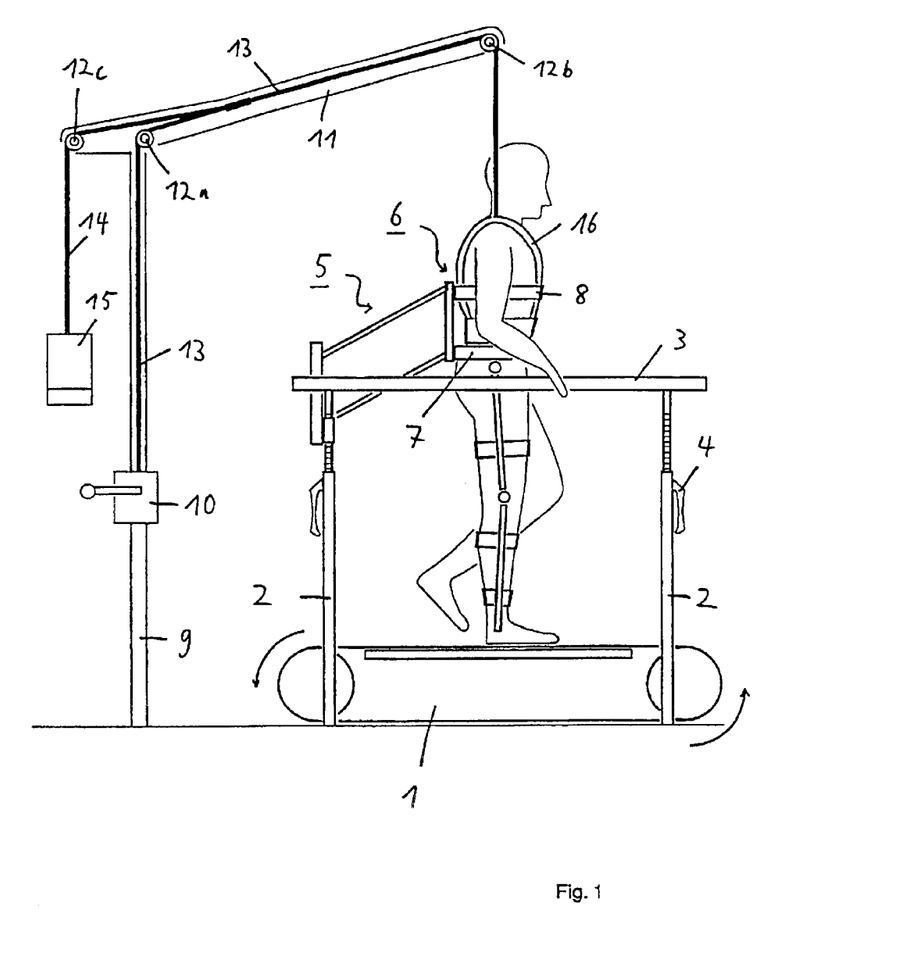
FIG. 1 shows a schematic portrayal of the principle of treadmill training with driven orthotic device, where the fixation is accomplished with a parallelogram.

FIG. 1 shows a schematic portrayal of the principle of the treadmill training system with driven orthotic device, in a variation with a parallelogram for stabilizing the patient. At each treadmill 1, one each rail 3 of a railing on supports 2 is mounted on each side of the walking surface, the rail being adjustable in height with a mechanism as is the case with a set of parallel hand rails. At the rear end of the rail 3, a parallelogram 5 that will be described in more detail later has been attached in a movable manner. The parallelogram 5 is used for stabilizing an orthotic device 6 that is designed to receive the patient and is located above the treadmill 1. The parallelogram 5 permits a movement of the orthotic device 6 only on a predetermined sector, whereby the movement is indicated by an arrow. This stabilizes both the orthotic device and the patient so that he is unable to tip either laterally, forward or backward. The patient's upper body is connected via a hip belt 7 and a chest belt 8 with the orthotic device 6 and is held in this way in a constant vertical position. The height adjustability of the rail 3 also makes it possible to adjust the height of the parallelogram 5. The parallelogram 5 also is automatically adjusted in height for patients of different heights when the rail 3 is adjusted.

Figure 2:
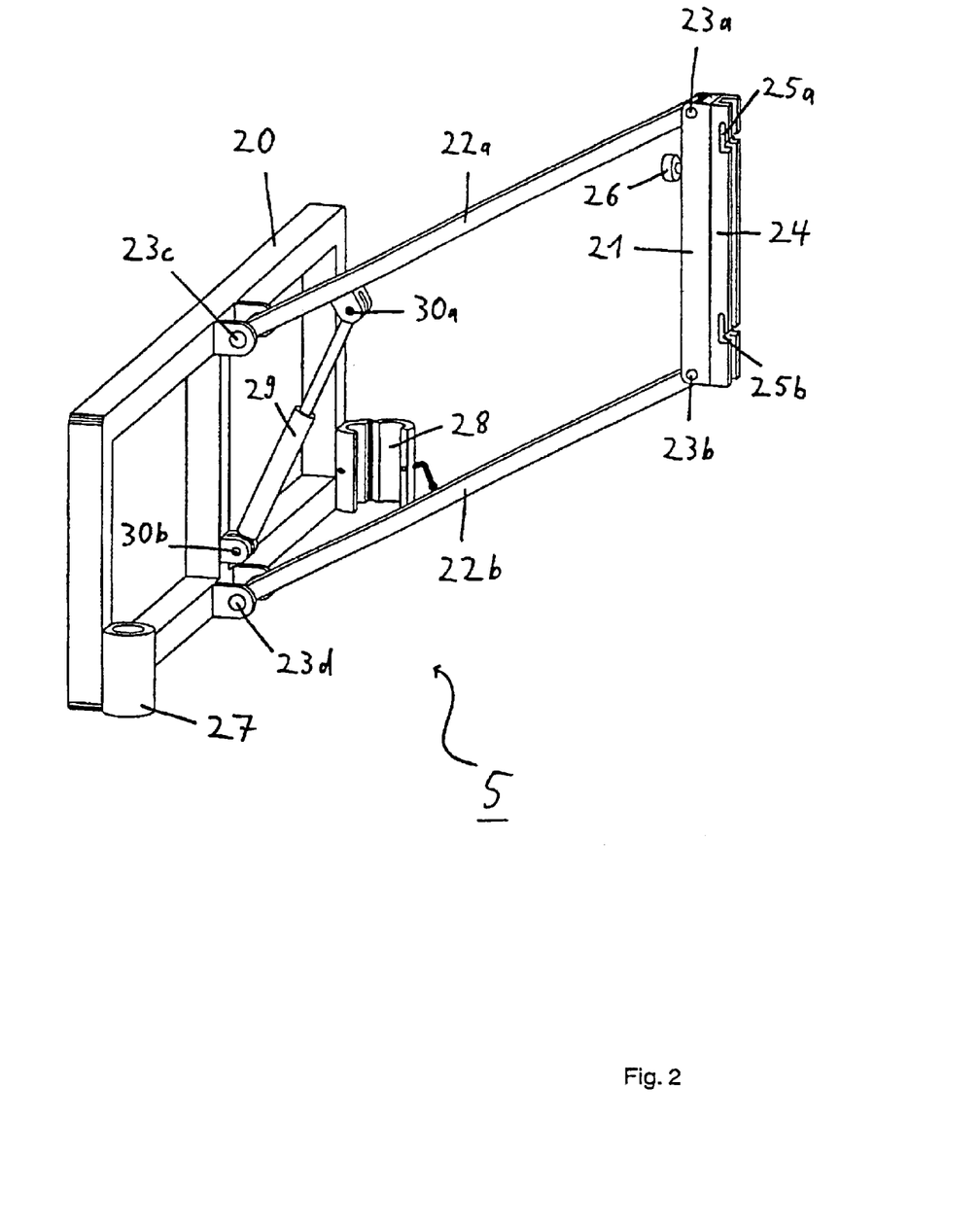
FIG. 2 shows the parallelogram for fixing the driven orthotic device on the treadmill.

Behind the treadmill 1, a suspension device comprising a support 9, cable hoist 10, jib 11, rollers 12a, 12b, and 12c, wire cables 13 and 14 and a variable counterweight 15 is also provided. From the cable hoist 10, the wire cable 13 is passed via rollers 12a and 12b to the patient. The latter is wearing a treadmill belt 16 to which the wire cable 11 is fastened. A second wire cable 14 that is fastened to the part of the wire cable 13 located between the rollers 12a and 12b is passed over the roller 12c, and a counter-weight 15 can be hung onto its end. When the therapy is started, the treadmill belt 16, which is used in the manner known from manual treadmill therapy, is put on the patient sitting in the wheel chair. The treadmill belt 16 is then hung with a spring hook onto the wire cable 13, and the patient is pulled up with the cable hoist 10. Once the patient is in an upright position, the counter weight 15 is attached, so that the patient is partially relieved of his own body weight during therapy. After this, the wire cable 13 can be slightly loosened again with the help of the cable hoist 10, after which the patient is able to walk on the treadmill under constant relief. The counter weight 15 is reduced during the course of the therapy, i.e., the load on the legs is gradually increased until the patient's legs are able to carry his entire weight., FIG. 2 shows the parallelogram 5 for fixing the driven orthotic device on the treadmill. The parallelogram consists of a frame-shaped base frame 20, an orthotic device part 21, two carriers 22a and 22b that connect the base frame 20 with the orthotic device part 21, and an orthotic device holder 24. The two carriers 22a and 22b are positioned in bearings 23a–23d in such a way that the orthotic part 21 can only move parallel to the base frame 20. On the orthotic device part 21, a U-shaped profile with guides 25a and 25b, which are constructed as L-shaped slits, is provided on the outside of the parallelogram of the orthotic device holders 24. The orthotic device is hung into these slits and fixed with a cam 26 (also see FIG. 6). By pulling out the cam 26, the orthotic device can be loosened and removed again.

The parallelogram 5 is fastened by means of a bearing 27 that is attached to the bottom part of the base frame 20 to a rail of the treadmill in such a way that it can be freely rotated horizontally. In this way the parallelogram can be rotated from the outside across the treadmill and can be fastened with a closure 28 that is attached on the side of the lower part of the base frame 20 facing the bearing 27 to the other side of the treadmill, again to the other rail. This makes it possible that the patient is able to drive or can be driven onto the treadmill with his wheel chair when the parallelogram is in the "opened" state. The parallelogram can be "closed" once the patient is lifted with the suspension device from his wheel chair and the wheel chair has been pushed off the treadmill. The it orthotic device, which has been fastened to the orthotic device holder 24, can be adapted and fixed to the patient. Between the base frame 20 and the top carrier 22a, a gas pressure nil spring 29 that compensates the weight of the orthotic device and the parallelogram is attached to bearings 30a and 30b by pushing the carrier 22a upward with a force necessary to move the orthotic device almost weightless along the parallelogram 5. Instead of the gas pressure spring 29, a mechanical spring can be attached at the same location in order to compensate the weight of the orthotic device.

Another option (not shown) for partially relieving the orthotic device of its weight consists of attaching a roller above the base frame 20, over which roller a wire cable is passed that is attached near the bearing 30a and is loaded on the other side of the parallelogram with a counter weight.

Figure 3:
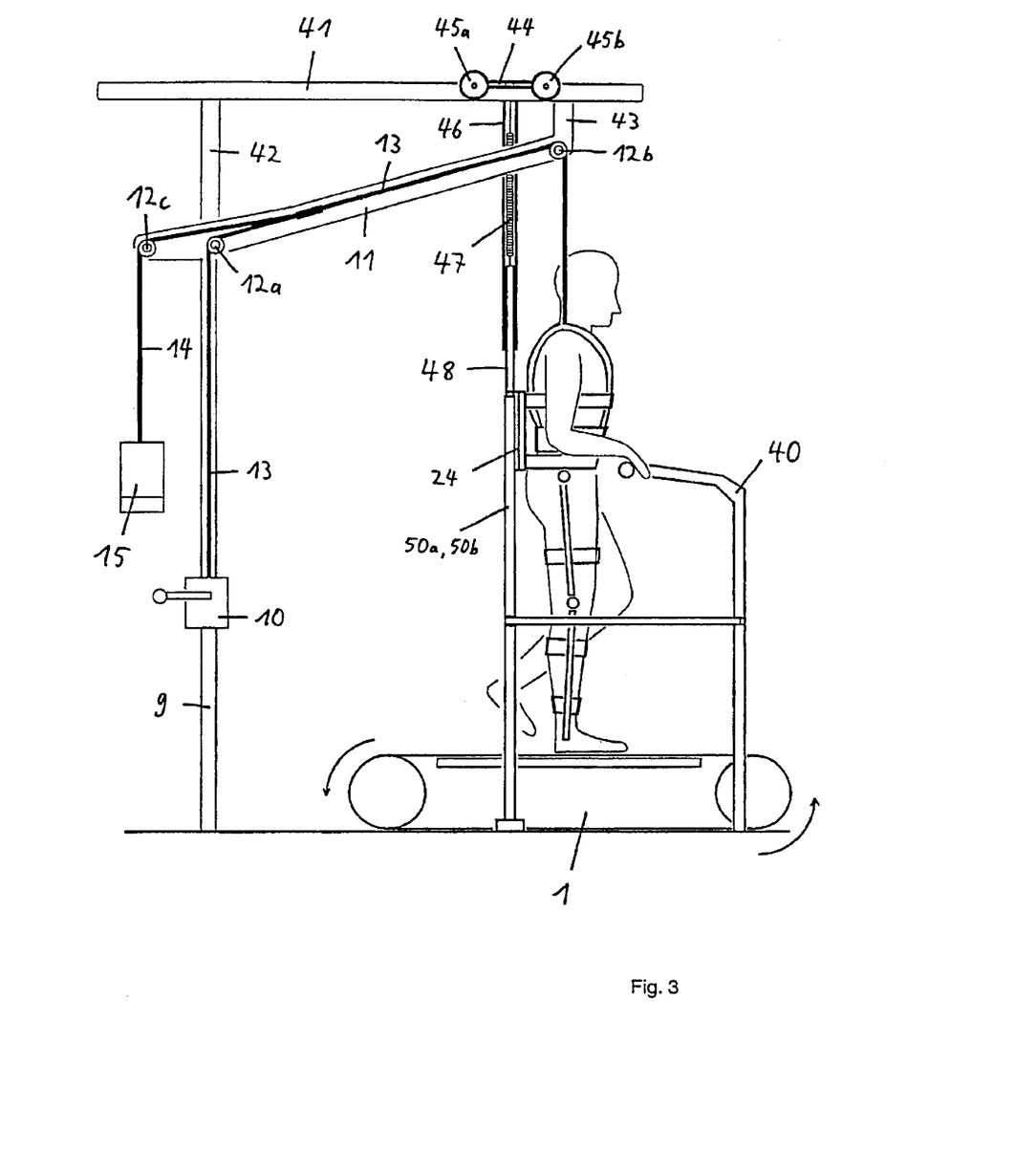
FIG. 3 shows a schematic portrayal of the principle of treadmill training with driven orthotic device, where the fixation is accomplished with a roller guide.

FIG. 3 shows a schematic of the principle of the treadmill training system with driven orthotic device in a variation with a roller guide for stabilizing the patient. This is an alternative to the stabilization described in reference to FIG. 1, whereby the solution for use with the driven orthotic device described in FIG. 1 should be preferred.

Another variation of the rail 40 that can be adjusted in height is mounted to the treadmill 1. As in the variation with the parallelogram, the suspension device consisting of support 9, cable hoist 10, jib 11, rollers 12a, 12b, and 12c, wire cables 13 and 14 and counter weight 15 is provided behind the treadmill 1.

A track 41 is attached with carriers 42 and 43 on the support 9 or the jib 11 above the treadmill 1. A cart 44 with two casters 45a and 45b is located on the track 41 and is able to move forward and backward on it. A guide tube 46 (rectangular tube) holding a spring 47 that is attached to the top end of the guide tube 46 is attached vertically downward on the cart 44. This spring pulls upward with a force that compensates the weight of the orthotic device. A rectangular tube 48 that fits into the guide tube 46 and in this way is guided by it is located at the lower end of the spring 47. The orthotic device holder 24 and a roller guide (see FIG. 4) are attached at the bottom end of the rectangular tube 48. A guide track 50a or 50b is attached to each side of the treadmill 1.

Figure 4:
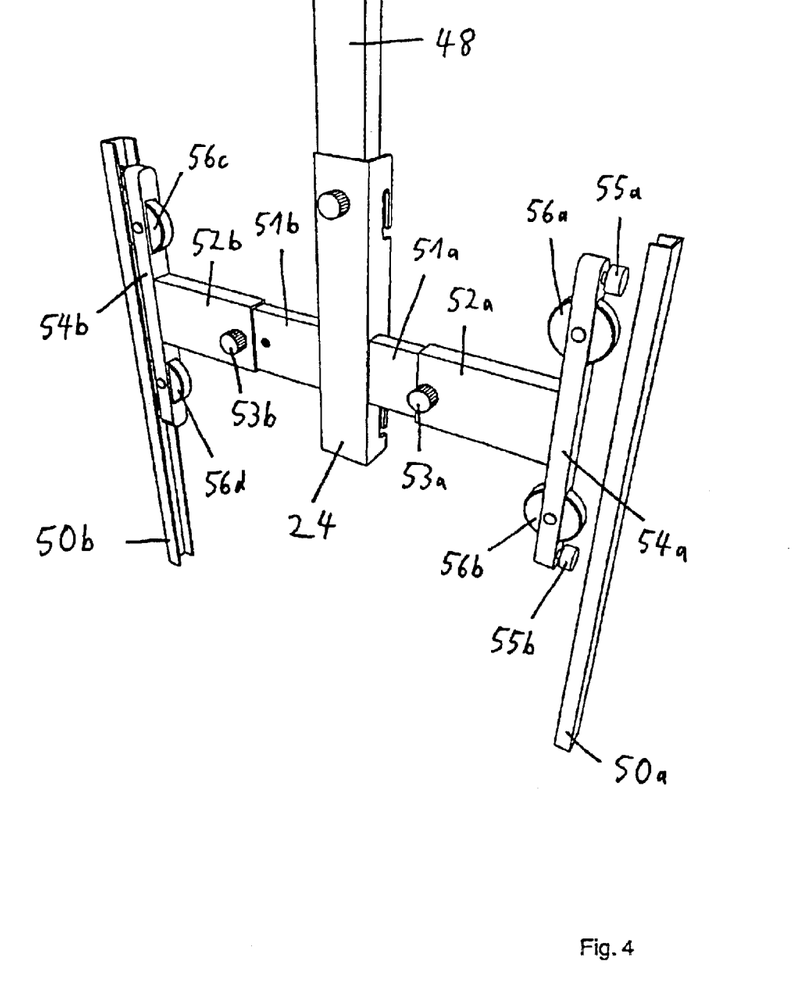
FIG. 4 shows the roller guide for fixing the driven orthotic device on the treadmill.

FIG. 4 shows the roller guide for stabilizing the driven orthotic device on the treadmill. At the bottom end of the rectangular tube 48 one is able to see the orthotic device holder 24, which again is provided on each side with a rectangular tube 51a or 51b arranged vertically in relation to the orthotic device holder 24. Two further rectangular tubes 52a and 52b that enclose tubes 51a and 51b can be fixed with snap-in mechanisms 53a and 53b in two different positions on tubes 51a and 51b. FIG. 4 shows the left side in the 'extended' and the right side in the 'retracted' state. The outer ends of tubes 52a and 52b are provided with roller holders 54a and 54b, to which again rollers 55a–55d and 56a–56d are attached. The rollers 55c and 55d cannot be seen in the figure. In the extended state of tubes 52a and 52b, the rollers 55a–55d as well as 56a–56d run in guide tracks 50a and 50b. Rollers 55a–55d ensure that the orthotic device, with the patient, is unable to tip forward or backward; rollers 56a–56d ensure lateral stability.

During therapy with the treadmill training system with driven orthotic device and a roller guide of this type for stabilizing the patient, the patient is suspended above the treadmill—as described in FIG. 2. The orthotic device is then moved towards the patient from the back, guided via the cart, and is adapted to him. Then tubes 52a and 52b are extended into the guide tracks 50a and 50b in order to stabilize the patient with rollers 55a–55d and rollers 56a–56d.

Figure 5:
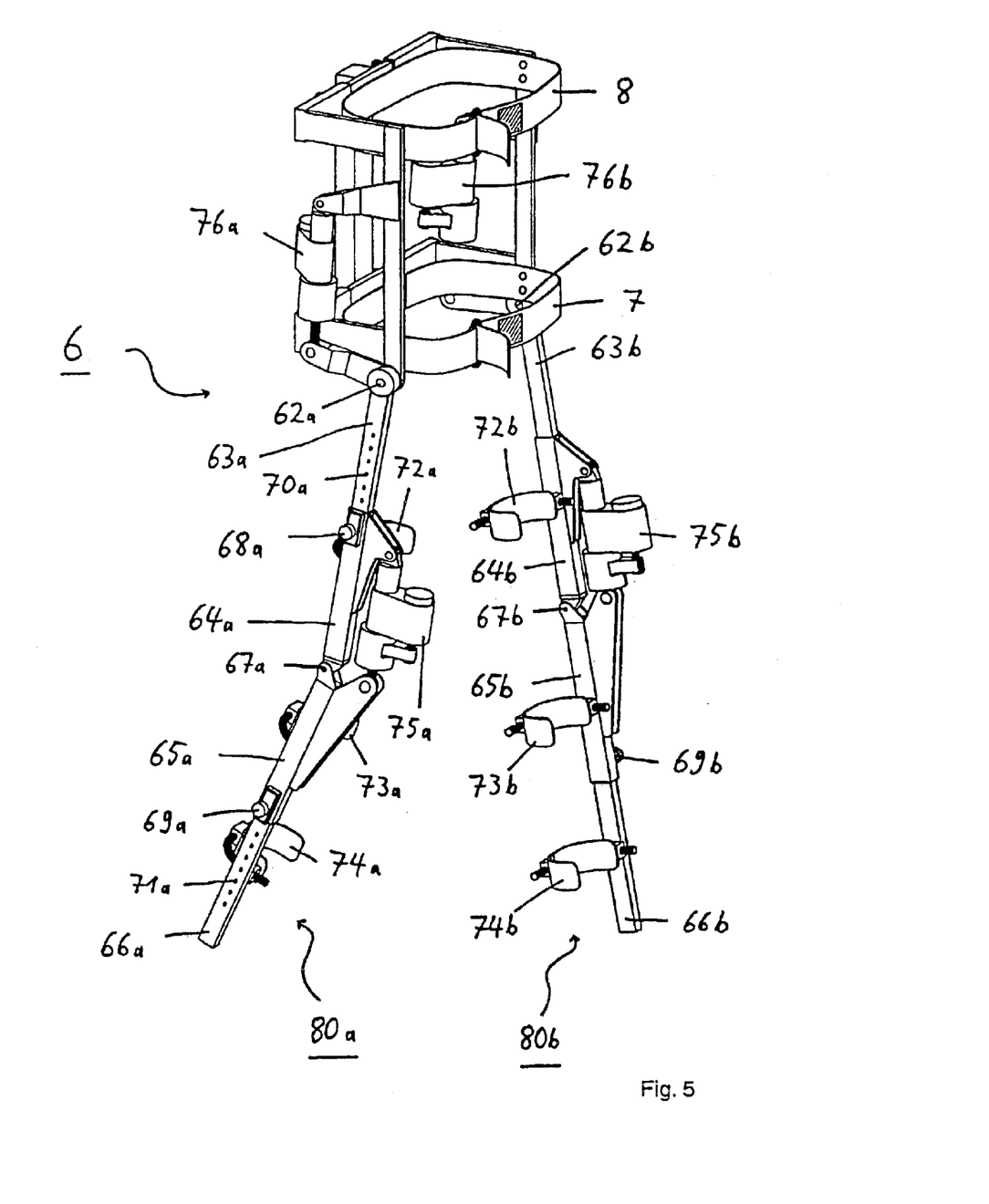
FIG. 5 shows an overall view of the driven orthotic device.

FIG. 5 shows an overview of the driven orthotic device 6. It consists essentially of a hip orthotic device (see FIG. 6) and two leg parts 80a and 80b. The hip orthotic device is an orthotic device with adjustable width that can be adapted to the patient and in which the upper body of the patient is fixed with the hip belt 7 and the chest belt 8. The belts 7 and 8 are relatively wide hook-and-loop belts with a closure in both the back and the front. Each side of the hip orthotic device is provided at its bottom part with a ball bearing 62a or 62b. The two leg braces 63a and 63b are attached to the latter in a movable manner. These bearings guide the leg braces 80a and 80b during walking on the treadmill in a plane parallel to the movement plane of the patient's legs. The hip orthotic device must be adapted to the patient in such a way that the hip joints of the patient are located directly below the bearing 62a or 62b.

The leg braces 63a, 63b, 64a, 64b, 65a, 65b, 66a, and 66b of leg parts 80a and 80b are constructed as rectangular tubes. The tubes 64a, 65a, and 64b, 65b enclose tubes 63a, 66a and 63b, 66b, and are connected with each other via the knee joints 67a and 67b. The tubes 63a, 63b and 64a, 64b, as well as 65a, 65b and 66a, 66b can be moved inside each other. The sliding surfaces between the tubes that have been pushed inside each other permit an easy adjustability of the leg lengths, that is, nevertheless, practically free from any play. At one end of each of the tubes 64a, 64b and 65a, 65b, a snap-in mechanism 68a, 68b (not visible) and 69a, 69b is attached, which fixes these pipes with a bolt inside the rows of holes 70a, 70b, and 71a, 71b provided in regular intervals in the tubes 63a, 63b, and 66a, 66b (neither of which is visible). In this way, the lengths of the leg parts 80a and 80b each are adapted to the leg lengths of the patient, and the position of the joints 67a and 67b can be matched with the knee joints of the patient. The holes are continuously numbered so that the size setting can be read, which is important for a quick fitting when a patient is treated repeatedly.

Angle sensors (potentiometers) that are used to control the orthotic device are integrated in the hip and knee joints 62a, 62b or 67a, 67b. The leg braces 80a and 80b are fastened with cuffs 72a, 72b, 73a, 73b and 74a, 74b to the patient's legs. The cuff pair 72a, 72b is attached on the track side to tubes 64a, 64b, the cuff pair 73a, 73b to tubes 65a, 65b, and the cuff pair 74a, 74b to tubes 66a, 66b.

Knee drives 75a, 75b and hip drives 76a, 76b are provided for moving the hip or, respectively, knee joints.

The leg braces 64a and 64b can be pulled completely out of leg braces 63a and 63b. The cables or electrical supply lines of the sensors and actuators below tracks 63a or 63b can be unplugged via a connector. In this way, each leg part can be removed individually from the driven orthotic device 6. This makes it possible to guide only one leg of a patient with hemiparesis actively and to let an otherwise healthy leg walk by itself (one leg therapy).

Figure 6:
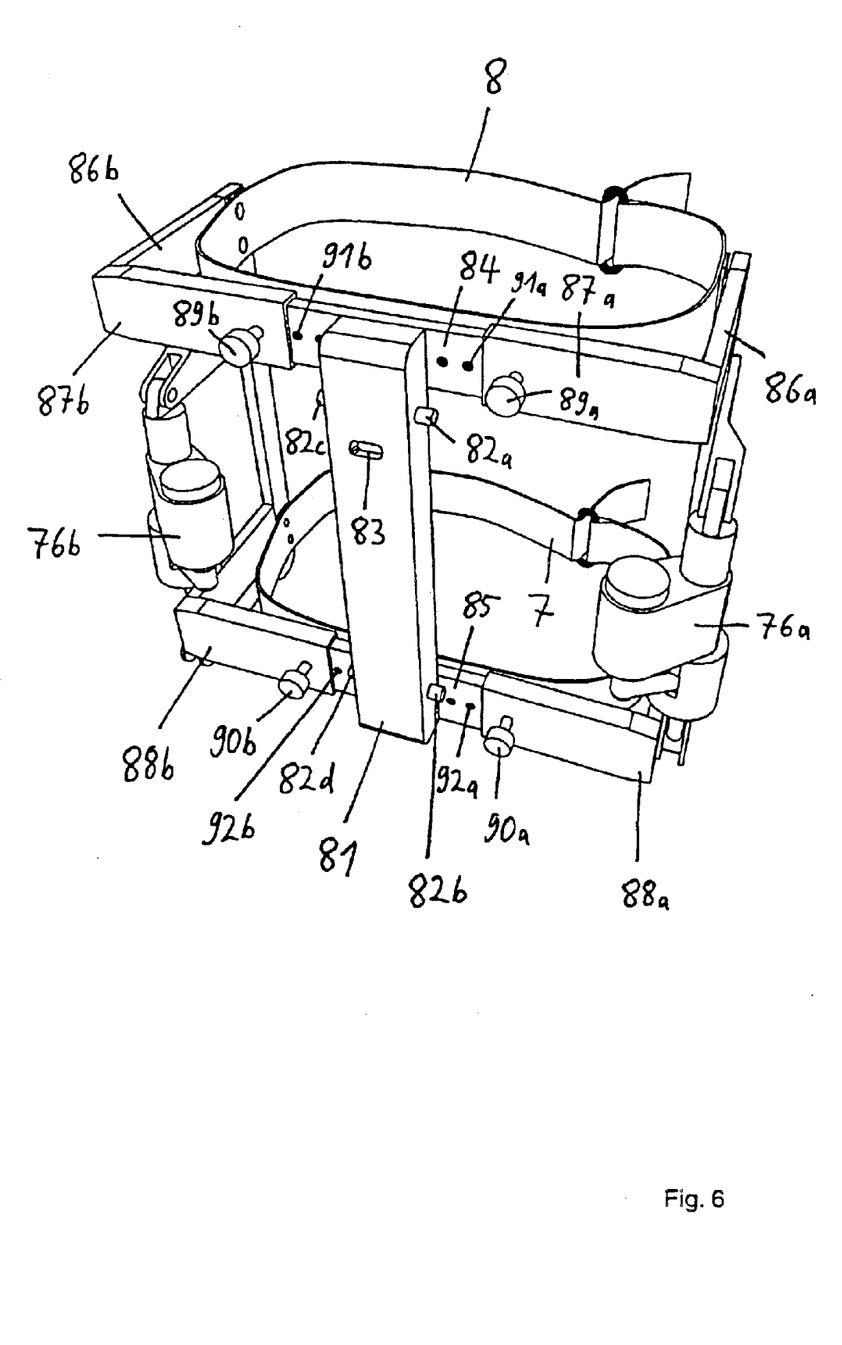
FIG. 6 shows a view of the adjustable hip orthotic device.

FIG. 6 schematically shows a hip orthotic device with adjustable width. An orthotic device back support 81 is fitted on each side with two bolts 82, 82b and 82c, 82d that make it possible to suspend the hip orthotic device in the guides of the orthotic device holder. The backside of the orthotic device back support 81 is provided with a stop hole 83 into which the cam of the orthotic device bolder can be snapped in order to fix the hip orthotic device in the orthotic device holder. Two rectangular tubes 84 and 85 are provided on the front of the orthotic device back support 81. Rectangular tubes 87a and 87b as well as 88a and 88b are also provided on the top and bottom of two hip side parts 86a and 86b and enclose the tubes 84 and 85 on one side each of the orthotic device back support and can be freely moved on the latter. The hip side parts 86a and 86b are fixed in the correct position with the snap-in mechanisms 89a and 89b as well as 90a and 90b, each of which can be snapped with a cam into the rows of holes 91a and 91b as well as 92a and 92b. In this way, the hip orthotic device can be adjusted to the individual requirements (hip width) of the patients by moving the hip side parts 86a and 86b. As a result of the rigid connection of the tubes 87a and 88a or, respectively, 87c and 88b through the hip side parts 86a and 86b, the snap-in mechanisms 89a and 90a or, respectively, 89b and 90b each must be released simultaneously in order to move one hip side part. On the inside of the hip side parts 86a and 86b, the hip belt 7 is in each case attached on the top inside, and the chest fax belt 8 on the bottom inside. The figure also shows the two hip drives 76a and 76b.

Figure 7:
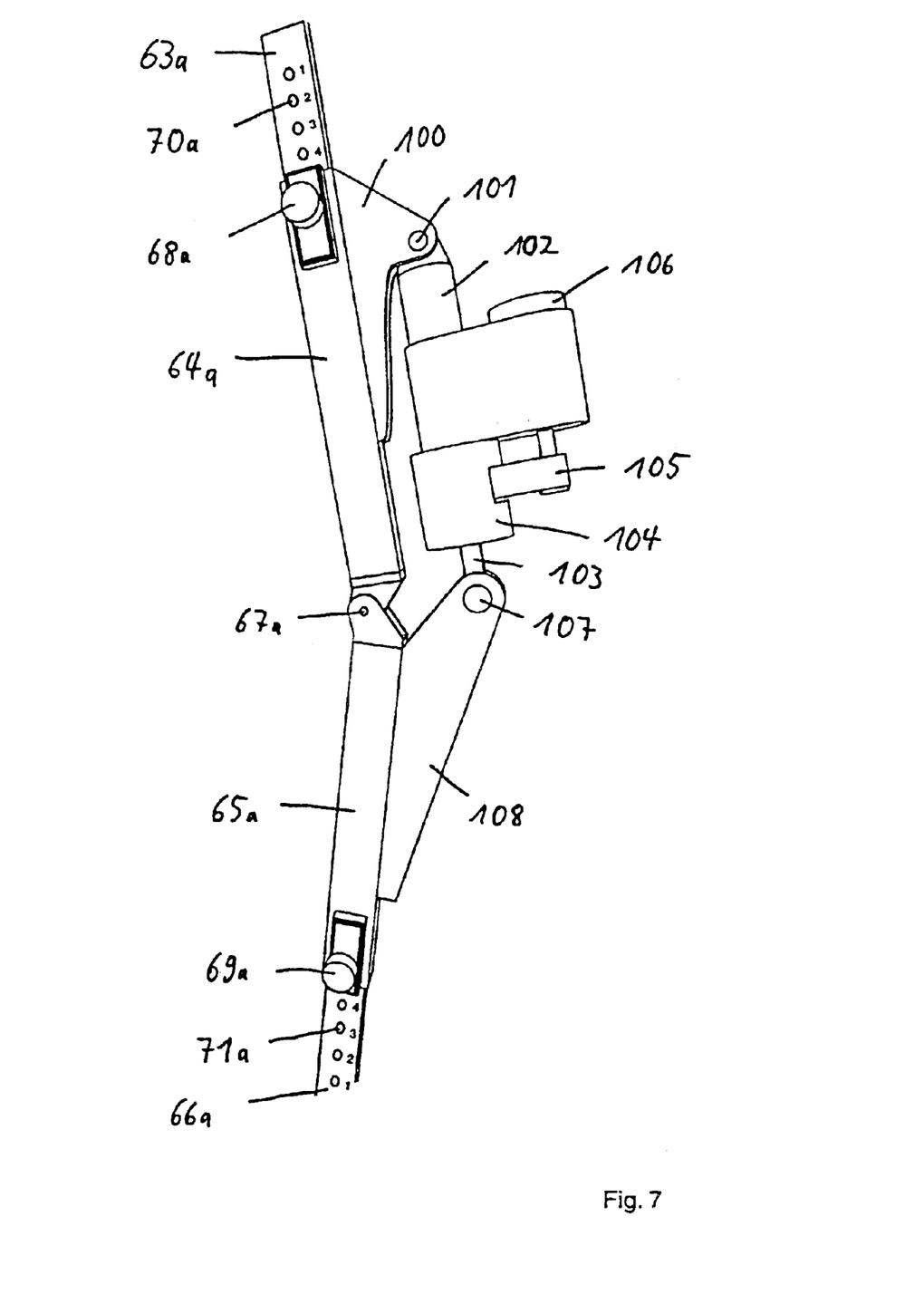
FIG. 7 shows an exemplary embodiment of a knee drive with ball screw spindle.

FIG. 7 shows an exemplary embodiment of a drive with a ball screw spindle for the right knee joint. A holder 100 is attached to the leg brace 64a. A bolt 101 is located on this holder 100. A guide cylinder 102 of the spindle drive is positioned via a roller bearing on this bolt 101. A ball screw spindle 103, which in this drawing is almost completely retracted, moves inside this guide cylinder 102. Located in the screw nut housing 104 is the ball screw spindle nut (not visible) that is positioned inside the housing so that it can be driven via a toothed V-belt 105 by an electric motor 106. The part of the ball screw spindle 103 extended from the guide cylinder 102 is positioned via a roller bearing on a bolt 107 that is fastened in a holder 108. The holder 108 is again connected tightly to the leg brace 65a.

The leg brace 64a is connected via ball bearing 67a in an articulated manner with the leg brace 65a. If the electric motor 106 rotates the spindle nut via the toothed V-belt 105, the ball screw spindle 103 ("stationary spindle") is rotated into or, respectively, out of the guide cylinder 102. This results in an extension or flexion of the leg orthotic device around bearing 67a.

At the top end of the leg brace 64a or at the bottom end of the leg brace 65a, the snap-in mechanisms 68a or 69a can be seen, as well as the numbered rows of holes 70a or, respectively, 71a arranged in tubes 63a or 66a, which are used for quickly fitting the length of the leg parts to the patient. The rows of holes 70a and 71a are provided with marks (numbers) so that the settings can be read off them. The settings are necessary for configuring a regulator. However, they also can be stored in order to correctly set the orthotic device for the patient at a later training session.

The same ball screw spindle drive is used in principle in the same manner to drive the left knee and both hip joints.

Figure 8A:
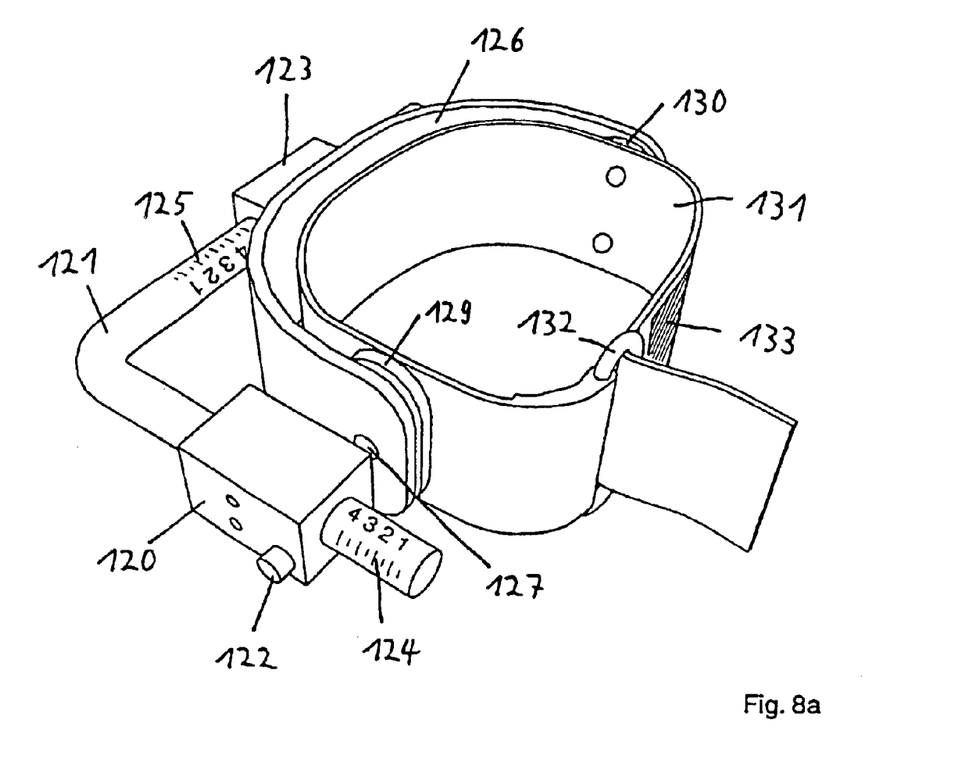
FIG. 8 shows an exemplary embodiment of a cuff for fixing the legs.
Figure 8B:
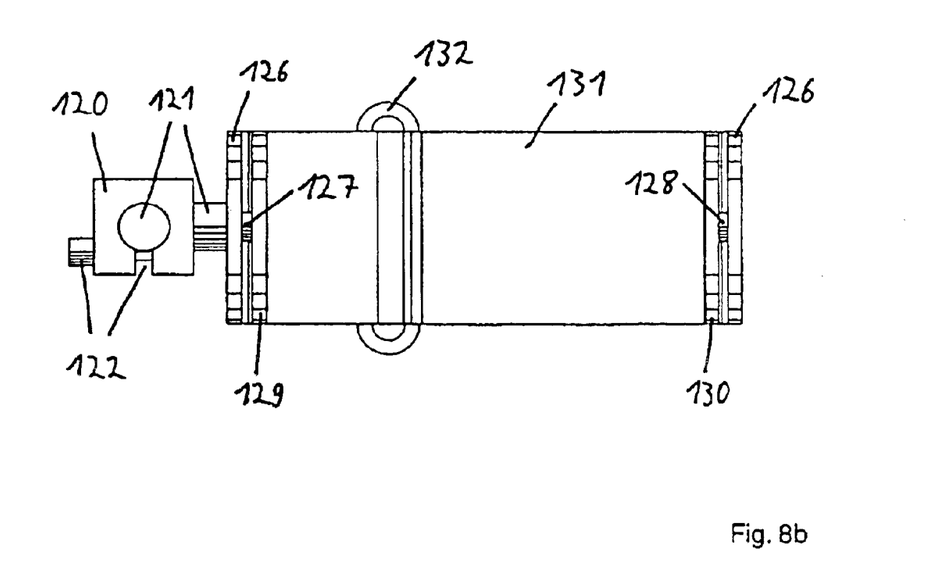

FIGS. 8a and 8b show a cuff for fixing the legs: FIG. 8a is a perspective view; FIG. 8b a frontal view. A holding mechanism 120, one of which is attached to each of the leg braces, is provided with a round opening into which a metal pipe 121 is passed. The metal pipe 121 can be freely moved inside the holding mechanism 120 and can be attached in the correct position with a quick-screw mechanism 122. On the other leg of the metal pipe 121, that is bent at a right angle, a second holding mechanism 123, that is identical with holding mechanism 120, is provided and can be moved, like the latter, freely on the pipe and be fixed in the correct position. In this way, the patient's legs can be positioned optimally in the orthotic device so that the movement planes as well as joint positions of the orthotic device and legs of the patients match. The positions in which the holders 120 and 123 are fixed on the pipe are marked with marks 124 and 125 so that the settings can be reconstructed at any time.

A rigid, half-round hoop 126 is screwed onto the holding mechanism 123. At each of the ends of this hoop 126, a bearing 127 and 128 is fixed. A small metal plate 129 and 130 is able to rotate freely in each of these bearings. At the inside of the small metal plates, a hook-and-loop tape 131 has been attached so that the rear part of the tape is closed on the hoop side, and front part is open. The length of the rear part has been selected so that the leg of a patient finds enough space inside the cuff, yet the tape does not touch the hoop 126 in the stretched state (when the leg is fixed in it). At the front, open part of the tape 131, a metal hoop 132 is attached on one end, through which the other end of the tape can be looped. In this way, the tape can be pulled tightly around the patient's leg and fixed with a hook-and-loop closure 133. These tapes, which are positioned in a rotatable manner, make it possible to distribute any forces that occur as uniformly as possible over the patient's skin when the leg orthotic device moves the patient's legs. The patient's leg does not come into contact with rigid parts of the orthotic device. This is important in order to prevent pressure ulcers.

It was found to be particularly advantageous that during the first adaptation of the orthotic device to a patient, all settings at the marks are read, that the values measured in this way are stored, and that during a later therapy session with the same patient the orthotic device is again set according to these values.

Figure 9:
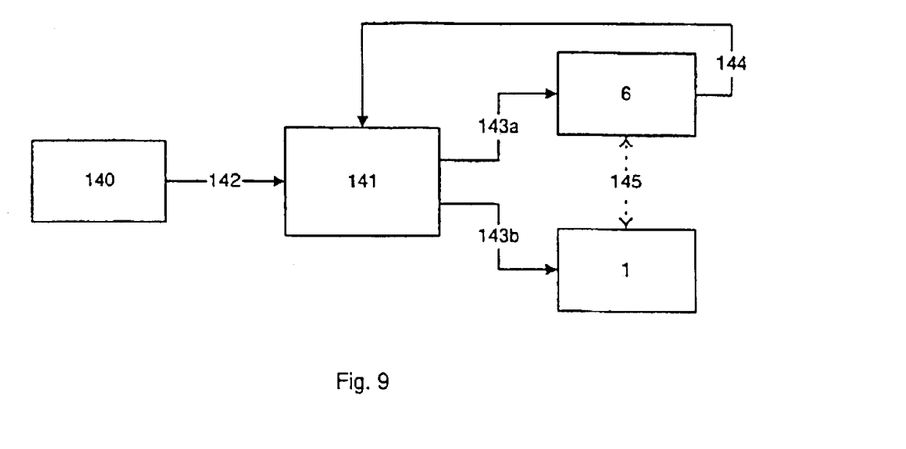
FIG. 9 shows an overview of the control of the therapy system.

FIG. 9 shows an overview of the control of the therapy system. The control consists of an input device 140, a control unit 141, the treadmill 1 and the driven orthotic device. The control unit 141 can be configured with the user data 142 via the input device 140. The control unit 141 is used to generate and control natural, i.e., physiological walking patterns in the orthotic device 6 and to control the treadmill 1. The orthotic device contains the desired position values for the knee and hip drives as control signals 143*a*. The measuring values of the angle sensors integrated in the knee and hip joints are returned as measuring values 144 to the control unit 141, creating a control circuit (141 143*a* 6 144 141) through which the leg position of the orthotic device 6 can be precisely controlled and synchronized with the treadmill speed. A control signal 143*b* is fed to the treadmill 1 and permits control of the treadmill speed that can be predetermined at the input device 140.

A central task of the control unit 141 is the synchronization of the sequence of movements of the orthotic device 6 with the treadmill speed: because of the orthotic device 6 driven at the knees and hip and the speed-controlled treadmill 1, a coupling 145 between the orthotic device 6 and the treadmill 1 is created during each standing phase and results in an overdetermination of the system that is eliminated by a synchronization of the leg movement with the treadmill speed.

Figure 10:
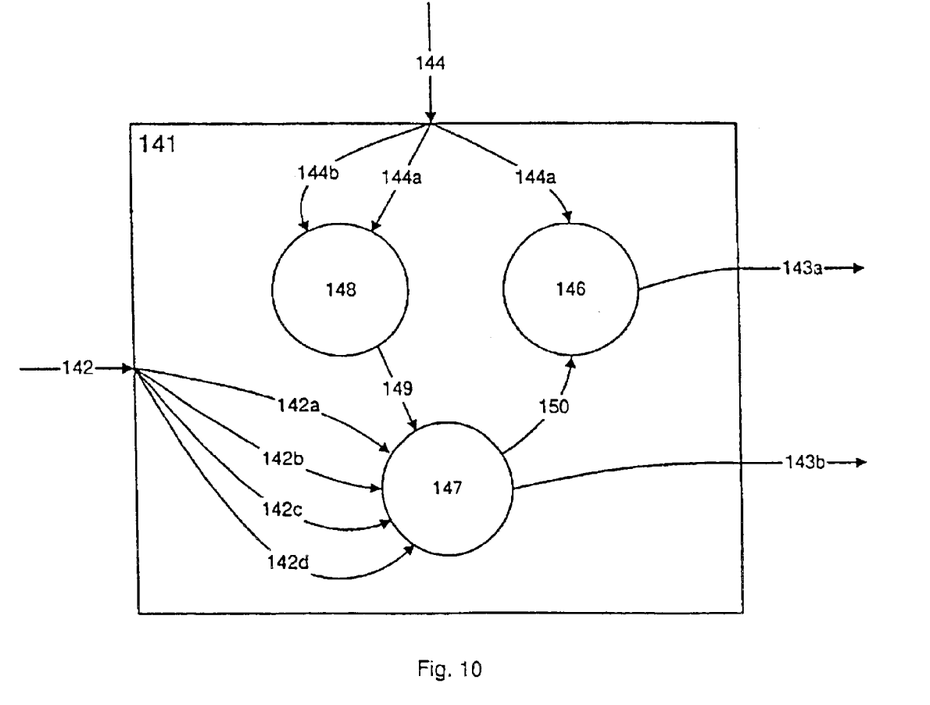
FIG. 10 shows the control unit.

FIG. 10 shows the control unit 141 in detail. The interfaces of the control unit 141 consist of the user data 142, control signals 143*a* and 143*b*, and measuring values 144. The user data 142 include a predetermined setting for the step length 142*a*, a predetermined setting for the treadmill speed 142*b*, as well as all patient-specific settings 142*c*, in particular the leg length set in the orthotic device. The user data 142 also include the desired movement curves 142*d* through which a walking pattern 150 to be created can be adapted optimally to the patient. The control signals 143*a* are connected to the knee and is, hip drives of the orthotic device and preset the desired position of the knee and hip joints. The control signal 143*b* permits the speed control of the treadmill. The measuring values 144 are divided into signals 144*a* of angle sensors that are integrated into the knee and hip joints of the orthotic device, and into signals 144*b* of foot switches that are often used in walking analysis and are integrated on or in the patient's shoes.

The user data 142 must be entered at the beginning of the therapy session or must be loaded from data storage into the control unit 141. For safety reasons, a change of the patient-specific settings 142*c* and desired movement curves 142*d* can only be performed when the orthotic device is standing still. In contrast, step length 142*a* and treadmill speed 142*b* also can be changed during operation of the driven orthotic device.

The central processes of the control unit 141 consist of a position regulator 146, a phase regulator 147, and a trigger unit 148. The position regulator 146 generates the control signals 143*a* that are fed as desired values for the leg position to the knee and hip drives of the orthotic device. The control circuit of the position regulator 146 is closed by feeding the measuring values 144*a* of the angle sensors of the orthotic device back, so that the leg position of the orthotic device can be precisely controlled. The phase regulator 147 is located together with the trigger unit 148 in a control circuit that is higher than the position regulator 146 and which, because of the predetermined treadmill speed 142*b* and mechanical settings of the orthotic device (patient-specific settings 142*c*) scales the desired movement curves 142*d* in such a way with respect to time that the predetermined step length 142*a* is on average reached as closely as possible, and the sequence of movement of the orthotic device is synchronized with the treadmill speed 142*b*: with a predetermined step length 142*a*, the swinging leg of the patient, i.e., the leg that is not standing on the treadmill, should always be set down at the same position on the treadmill. The change from the swinging to the standing leg and vice versa is reported to the phase regulator 147 by the trigger signal 149 that originates in the trigger unit 148. The trigger unit 148 receives the information necessary for this from the measuring values 144, i.e., from signals 144*a* of the leg position of the orthotic device (knee and hip angle) as well as from signals 144*b* of the foot switches. The walking pattern 150 calculated in this way in the phase regulator 147 is made available to the position regulator 146, and is used as a predetermined value for the leg position, and is further supplied via control signals 143*a* to the orthotic device.

What is claimed is:

1. Apparatus for treadmill training of walking-disabled patients, comprising a treadmill, a relief mechanism for the patient, and a driven orthotic device, wherein a parallelogram fixed in a height-adjustable manner on the treadmill is provided for stabilizing the orthotic and preventing the patient from tipping forward, backward and sideward, the parallelogram being attached to the orthotic device; the orthotic device comprises a hip orthotic device and two leg parts, whereby two hip drives are provided for moving the hip orthotic device, and two knee drives are provided for moving the leg parts; the hip orthotic device and leg parts are adjustable, the leg parts are provided with cuffs which are adjustable in size and position; and a control unit is provided for controlling the movements of the orthotic device and controlling the speed of the treadmill.

2. Apparatus as claimed in claim 1, wherein the parallelogram comprises a base frame, an orthotic device part, and two carriers that are interconnected via bearings; on the base frame, on the one lower side, a first bearing element is attached, with which first bearing element the base frame or, respectively, the parallelogram is positioned in a rotatable manner and is fixed on a first rail of a railing of the treadmill in a height-adjustable manner; on the base frame on the other lower side a second bearing element that can be flipped open and closed is attached, with which second bearing element the base frame or, respectively, the parallelogram can be locked to a second rail of the railing of the treadmill after the completed rotating movement around the first bearing element; and an orthotic device holder that is provided with means for attaching the orthotic device is attached to the orthotic device part.

3. Apparatus as claimed in claim 1, wherein a relief mechanism is attached to the parallelogram for compensating the weight of the orthotic device, whereby a gas pressure spring, a counter weight, or a mechanical spring is provided for this purpose.

4. Apparatus as claimed in claim 1, wherein the hip orthotic device is adjustable in its width.

5. Apparatus as claimed in claim 1, wherein the leg parts comprise leg braces that can be moved inside each other so that the leg parts are adjustable in length.

6. Apparatus as claimed in claim 1, wherein the leg parts are provided with cuffs that can be adjusted continuously 'anterior-posterior' and 'medial-lateral'.

7. Apparatus as claimed in claim 1, wherein the cuffs comprise a semi-round hoop and a tape; and a the tape is attached to the hoop in such a way that it can be freely wound around a rotary axis in a center of the patient's leg.

8. Apparatus as claimed in claim 7, wherein different settings of the orthotic device, including hip width, leg lengths, and cuff positions, are marked with marks.

9. Apparatus as claimed in claim 1, wherein a control unit is provided for controlling the drives of the orthotic device, the input values of said control unit being user data, the output values of the control unit being control signals for the orthotic device and the treadmill, and the control value of the control unit being measuring values.

10. Method for operating an apparatus as claimed in claim 1, wherein the orthotic device is turned away from the treadmill in order to permit the patient to gain access to the treadmill; the orthotic device is positioned above the treadmill and is fixed to the patient, whereby the orthotic device is relieved by a relief mechanism; and the orthotic device is driven and controlled, and the treadmill is driven and controlled.

11. Method as claimed in claim 10, wherein the parallelogram is positioned with the orthotic device at the railing of the treadmill in such a way that it can be opened towards the back, whereupon the patent is driven in a wheel chair onto the treadmill; the patient is secured in a treadmill belt or hung above the treadmill; and then the orthotic device is rotated from the back at the parallelogram onto the treadmill and is tightened on the suspended patient.

12. Method as claimed in claim 10, wherein the drives of the orthotic device are controlled by the control unit in such a way that the legs of the patient are moved in a natural, physiological walking pattern on the treadmill, whereby desired curves necessary for creating physiological sequences of movement are adapted by the control unit based on entered patient-specific settings and respective measuring values.

13. Method as claimed in claim 10, wherein the movements of the orthotic device are synchronized with the treadmill speed.

14. Method as claimed in claim 10, wherein the control unit synchronizes the movement of the legs with or adapts it to the speed of the treadmill in that a trigger unit signals the beginning of a standing phase and a course of a sequence of movements over time with a trigger signal, and desired curves are output to the drives of the orthotic device, adapted appropriately as control signals.

15. Method as claimed in claim 10, wherein settings of the adjustable orthotic device are read at markings, stored, and reconstructed.

16. Apparatus for treadmill training of walking-disabled patients, comprising a treadmill including a railing, a relief mechanism for the patient, and a driven orthotic device, wherein means for stabilizing the orthotic device are provided that prevent the patient from tipping forward, backward and sideward; the orthotic device comprises a hip orthotic device and two lea parts, two hip drives are provided for moving the hip orthotic device, and two knee drives are provided for moving the leg parts; a ball screw spindle drive is provided for each knee drive and hip drive, the orthotic device and leg parts are adjustable, the leg parts are provided with cuffs which are adjustable in size and position; and a control unit is provided for controlling the movements of the orthotic device and controlling the speed of the treadmill.

* * * * *